(12) United States Patent
Parthasaradhi et al.

(10) Patent No.: US 7,300,938 B2
(45) Date of Patent: Nov. 27, 2007

(54) POLYMORPHS OF IMATINIB MESYLATE

(75) Inventors: Reddy Bandi Parthasaradhi, Hyderabad (IN); Reddy Kura Rathnakar, Hyderabad (IN); Reddy Rapolu Raji, Hyderabad (IN); Reddy Dasari Muralidhara, Hyderabad (IN); Reddy Kesireddy Subash Chander, Hyderabad (IN)

(73) Assignee: Hetero Drugs Limited, Hyderabad (IN)

( * ) Notice: Subject to any disclaimer, the term of this patent is extended or adjusted under 35 U.S.C. 154(b) by 596 days.

(21) Appl. No.: 10/518,213

(22) PCT Filed: Jun. 2, 2003

(86) PCT No.: PCT/IN03/00206

§ 371 (c)(1), (2), (4) Date: Dec. 16, 2004

(87) PCT Pub. No.: WO2004/106326

PCT Pub. Date: Dec. 9, 2004

(65) Prior Publication Data

US 2005/0234069 A1      Oct. 20, 2005

(51) Int. Cl.
*C07D 401/14* (2006.01)
*A61K 31/506* (2006.01)
(52) U.S. Cl. .................. 514/252.18; 544/295
(58) Field of Classification Search ............... 544/295; 514/252.18
See application file for complete search history.

(56) References Cited

U.S. PATENT DOCUMENTS 5,521,184 A    5/1996   Zimmermann

FOREIGN PATENT DOCUMENTS

WO    WO 99 03854    1/1999

OTHER PUBLICATIONS

PCT International Search Report dated Jun. 2, 2003.

*Primary Examiner*—Deepak Rao
(74) *Attorney, Agent, or Firm*—Caesar, Rivise, Bernstein, Cohen & Pokotilow, Ltd.

(57) ABSTRACT

The present invention relates to novel polymorphs of imatinib mesylate, to processes for their preparation and to pharmaceutical compositions containing them.

24 Claims, 2 Drawing Sheets

POLYMORPHS OF IMATINIB MESYLATE

This application is a 371 of PCT/IN03/00206 filed Jun. 2, 2003.

FIELD OF THE INVENTION

The present invention relates to novel polymorphs of imatinib mesylate, to processes for their preparation and to pharmaceutical compositions containing them.

BACKGROUND OF THE INVENTION

Imatinib, chemically 4-[(4-methyl-1-piperazinyl)methyl]-N-[4-methyl-3-[[4-(3 -pyridinyl)-2-pyrimidinyl]amino]phenyl]benzamide, is represented by the following structure:

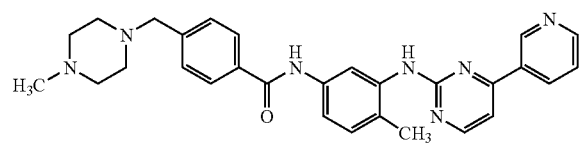

Imatinib and its salts are anti-tumor agents, which were disclosed in U.S. Pat. No. 5,521,184. Two crystalline modifications (α-form and β-form) of imatinib mesylate were mentioned in WO 99/03854.

WO 99/03854 mentioned amorphous imatinib mesylate, but it did not make any reference to hydrate of imatinib mesylate.

We have discovered a stable novel crystalline form of imatinib mesylate. The novel form is at least as stable as the reported forms, α- and β-forms. The novel crystalline form is stable over the time and has good flow properties and so, the novel crystalline form is suitable for formulating imatinib mesylate.

Amorphous forms of pharmaceutical products are usually known to have better dissolution properties than their crystalline forms. If amorphous form of a pharmaceutical product is stable enough, it can be formulated to a pharmaceutical composition having good dissolution properties.

We have discovered hydrate of imatinib mesylate.

We have also discovered a sufficiently stable non-hygroscopic amorphous form of imatinib mesylate hydrate. So, amorphous form of imatinib mesylate hydrate can be utilized to prepare stable pharmaceutical dosage forms having good dissolution properties.

One object of the present invention is to provide a stable novel crystalline form of imatinib mesylate, hydrate of imatinib mesylate and amorphous imatinib mesylate hydrate.

Another object of the present invention is to provide processes for preparing the novel crystalline form of imatinib mesylate, hydrate of imatinib mesylate and amorphous imatinib mesylate hydrate.

Still another object of the present invention is to provide pharmaceutical compositions containing the novel crystalline form of imatinib mesylate, hydrate of imatinib mesylate and amorphous imatinib mesylate hydrate.

DETAILED DESCRIPTION OF THE INVENTION

As used herein, room temperature refers to about 25° C. to 30° C.

In accordance with the present invention, there is provided a novel crystalline form of imatinib mesylate, designated as form H1, characterized by an x-ray powder diffraction spectrum having peaks expressed as 2θ at about 9.9, 11.1, 16.3, 17.3, 18.1, 19.1, 19.6, 20.3, 21.1, 21.9, 23.2, 23.6, 24.2, 24.9, 25.6, 26.0, 27.3, 27.9, 28.9, 29.4, 30.4 and 30.5 degrees. FIG. 1 shows typical form H1 x-ray powder diffraction spectrum.

In accordance with the present invention, a process is provided for preparation of imatinib mesylate form H1. Imatinib free base is dissolved in a chlorinated solvent, methanesulfonic acid is added and imatinib mesylate form H1 is isolated.

Examples of chlorinated solvents are chloroform, methylene dichloride, ethylene dichloride and a mixture thereof. Preferable solvents are chloroform and methylene dichloride.

Imatinib free base may be dissolved in the chlorinated solvents at room temperature or at an elevated temperature.

The quantity of methanesulfonic acid per mole of imatinib free base is not critical but preferably at least one mole of methanesulfonic acid per mole of imatinib free base is used to obtain maximum yield of imatinib mesylate.

Methanesulfonic acid can be added to the solution of imatinib free base in chlorinated solvent preferably between about 5° C. to reflux temperature, more preferably between room temperature to reflux temperature. Most preferably, methanesulfonic acid is added at room temperature.

Then, the precipitated imatinib mesylate form H1 is collected by filtration or centrifugation.

In accordance with the present invention, an another process is provided for preparation of imatinib mesylate form H1. A mixture of imatinib mesylate and a chlorinated solvent is stirred for about 10 hours to 48 hours and imatinib mesylate form H1 is isolated.

Examples of chlorinated solvents are chloroform, methylene dichloride, ethylene dichloride and a mixture thereof. Preferable solvents are chloroform and methylene dichloride.

Imatinib mesylate in a previously known crystalline or amorphous form may be used in the process. Imatinib mesylate hydrate obtained by the process described below may also be used. Particularly α-form, β-form or amorphous imatinib mesylate may be used.

Preferably, the mixture of imatinib mesylate and a chlorinated solvent is stirred between about 5° C. to reflux temperature, more preferably between room temperature to reflux temperature, for about 24 hours to 48 hours.

Then imatinib mesylate form H1 is collected by filtration or centrifugation.

In accordance with the present invention, there is provided a novel hydrate of imatinib mesylate. The water content of the hydrate of imatinib mesylate is between 2.0 to 3.2% by weight of hydrate of imatinib mesylate, typically between 2.2 to 2.9% by weight of hydrate of imatinib mesylate.

The amorphous form of imatinib mesylate hydrate, designated as amorphous imatinib mesylate hydrate, is characterized by having broad x-ray diffraction spectrum as in FIG. 2.

In accordance with the present invention, a process is provided for preparation of imatinib mesylate hydrate.

Imatinib mesylate hydrate is prepared by dissolving imatinib mesylate in a mixture of a suitable solvent and water and removing the solvents from the solution.

Imatinib mesylate in a crystalline or amorphous form may be used in the process. Particularly α-form, β-form or amorphous imatinib mesylate may be used.

The suitable solvent is selected from the group consisting of alcohols, e.g., methanol, ethanol, isopropyl alcohol; ketones, e.g., acetone; acetonitrile; and a mixture thereof.

The solvent may be removed from the solution by vacuum drying or spray drying to give amorphous imatinib mesylate hydrate. The drying time and the drying temperature depend on the solvent used in the process. For example if the solvent is methanol, the solvent and water can be removed at about 50° C. for about 9 hours.

Imatinib free base and imatinib mesylate obtained by the previously known methods may be used in the above processes.

In accordance with the present invention, there is provided a pharmaceutical composition comprising imatinib mesylate form H1 and a pharmaceutically acceptable carrier or diluent.

In accordance with the present invention, there is provided a pharmaceutical composition comprising imatinib mesylate hydrate and a pharmaceutically acceptable carrier or diluent. Amorphous imatinib mesylate hydrate may also be used in the composition.

Figure 1:
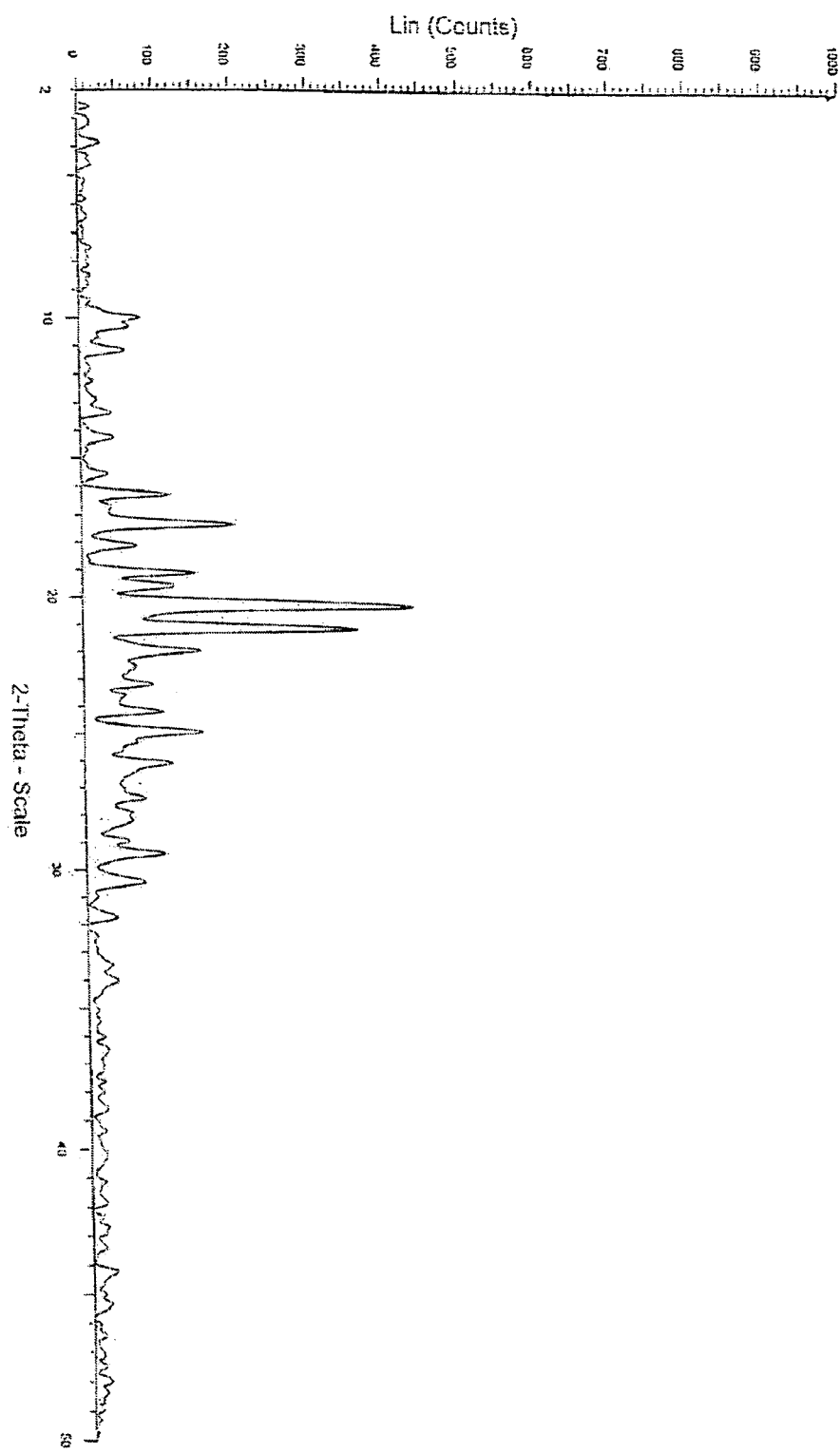
FIG. 1 is a x-ray powder diffraction spectrum of imatinib mesylate form H1.

x-Ray powder diffraction spectrum was measured on a Bruker axs D8 advance x-ray powder diffractometer having a copper-Kα radiation.

The invention will now be further described by the following examples, which are illustrative rather than limiting.

EXAMPLE 1

Imatinib free base (5.0 gm) is dissolved in chloroform (50 ml) at room temperature and then methanesulfonic acid (0.75 ml) is added. The contents are stirred for 5 hours at room temperature and separated crystals are filtered and dried to give 5.0 gm of imatinib mesylate form H1.

EXAMPLE 2

The mixture of Imatinib mesylate (α-form, 5.0 gm) and chloroform (150 ml) is heated to 50° C. and stirred for 36 hours at this temperature. Then the contents are cooled to 25° C., maintained for 5 hours at room temperature and filtered and dried to give 4.5 gm of imatinib mesylate form H1.

EXAMPLE 3

The mixture of Imatinib mesylate (β-form, 5.0 gm) and chloroform (150 ml) is heated to 50° C. and stirred for 36 hours at this temperature. Then the contents are cooled to 25° C., maintained for 5 hours at room temperature and filtered and dried to give 4.3 gm of imatinib mesylate form H1.

EXAMPLE 4

Imatinib free base (5.0 gm) is dissolved in methylene dichloride (50 ml) at room temperature and then methanesulfonic acid (0.75 ml) is added. The contents are stirred for 5 hours at room temperature and filtered and dried to give 4.9 gm of imatinib mesylate form H1.

EXAMPLE 5

The mixture of Imatinib mesylate (5.0 gm) and methylene dichloride (150 ml) is heated to 50° C. and stirred for 5 hours at this temperature. Then the contents are cooled to 25° C., maintained for 25 hours at room temperature and filtered to give 4.6 gm of imatinib mesylate form H1

EXAMPLE 6

Imatinib mesylate form H1 (3.5 gm) is dissolved in a mixture of methanol (25 ml) and water (5.0 ml) at room temperature. The solution is subjected to vacuum drying at about 50° C. for 9 hours to give 3.0 gm of amorphous imatinib mesylate hydrate.

EXAMPLE 7

Example 6 is carried out using imatinib mesylate (α-form) instead of imatinib mesylate form H1 to give imatinib mesylate hydrate.

EXAMPLE 8

Example 6 is carried out by subjecting the solution to spray drying instead of vacuum drying to give amorphous imatinib mesylate hydrate.

We claim:

1. A crystalline imatinib mesylate form H1, characterized by an x-ray powder diffraction spectrum having peaks expressed as 2θ at about 9.9, 11.1, 16.3, 17.3, 18.1, 19.1, 19.6, 20.3, 21.1, 21.9, 23.2, 23.6, 24.2, 24.9, 25.6, 26.0, 27.3, 27.9, 28.9, 29.4, 30.4 and 30.5 degrees.

2. The crystalline imatinib mesylate form H1 as defined in claim 1, further characterized by a x-ray powder diffraction spectrum as in FIG. 1.

3. A process for preparation of imatinib mesylate form H1 as defined in claim 1, which comprises the steps of:
   a) dissolving imatinib free base in a chlorinated solvent;
   b) adding methanesulfonic acid; and
   c) isolating imatinib mesylate form H1 by filtration or centrifugation;

wherein the chlorinated solvents is selected from chloroform, methylene dichloride, ethylene dichloride and a mixture thereof.

4. The process according to claim 3, wherein the chlorinated solvent is chloroform.

5. The process according to claim 3, wherein the chlorinated solvent is methylene dichloride.

6. A process for preparation of imatinib mesylate form H1 as defined in claim 1, which comprises the steps of:
   a) mixing imatinib mesylate and a chlorinated solvent; and
   b) isolating imatinib mesylate form H1 by filtration or centrifugation;

wherein the chlorinated solvent is selected from chloroform, methylene dichloride, ethylene dichloride and a mixture thereof.

7. The process according to claim 6, wherein the chlorinated solvent is chloroform.

8. A The process according to claim 6, wherein the chlorinated solvent is methylene dichloride.

9. Imatinib mesylate hydrate.

10. Imatinib mesylate hydrate of claim 9, wherein water content of the hydrate of imatinib mesylate is between about 2.0 to about 3.2% by weight of hydrate of imatinib mesylate.

11. Imatinib mesylate hydrate of claim 10, wherein water content of the hydrate of imatinib mesylate is between about 2.2 to about 2.9% by weight of hydrate of imatinib mesylate.

12. Imatinib mesylate hydrate of claim 11, wherein water content of the hydrate of imatinib mesylate is about 2.5% by weight of hydrate of imatinib mesylate.

13. A process for preparation of imatinib mesylate hydrate of claim 9, which comprises the steps of:
  a) dissolving imatinib mesylate in a mixture of a suitable solvent and water;
  b) removing the solvents from the solution formed in (a) either by vacuum drying or by spray drying;
wherein the suitable solvent is selected from alcohols, ketones, acetonitrile and a mixture thereof.

14. The process according to claim 13, wherein the solvent is removed by vacuum drying.

15. The process according to claim 13, wherein the solvent is removed by spray drying.

16. The process according to claim 13, wherein the alcohol is selected from methanol, ethanol and isopropyl alcohol; and the ketone is acetone.

17. The process according to claim 13, wherein the suitable solvent is methanol.

18. The process according to claim 13, wherein the suitable solvent is ethanol.

19. Amorphous imatinib mesylate hydrate.

Figure 2:
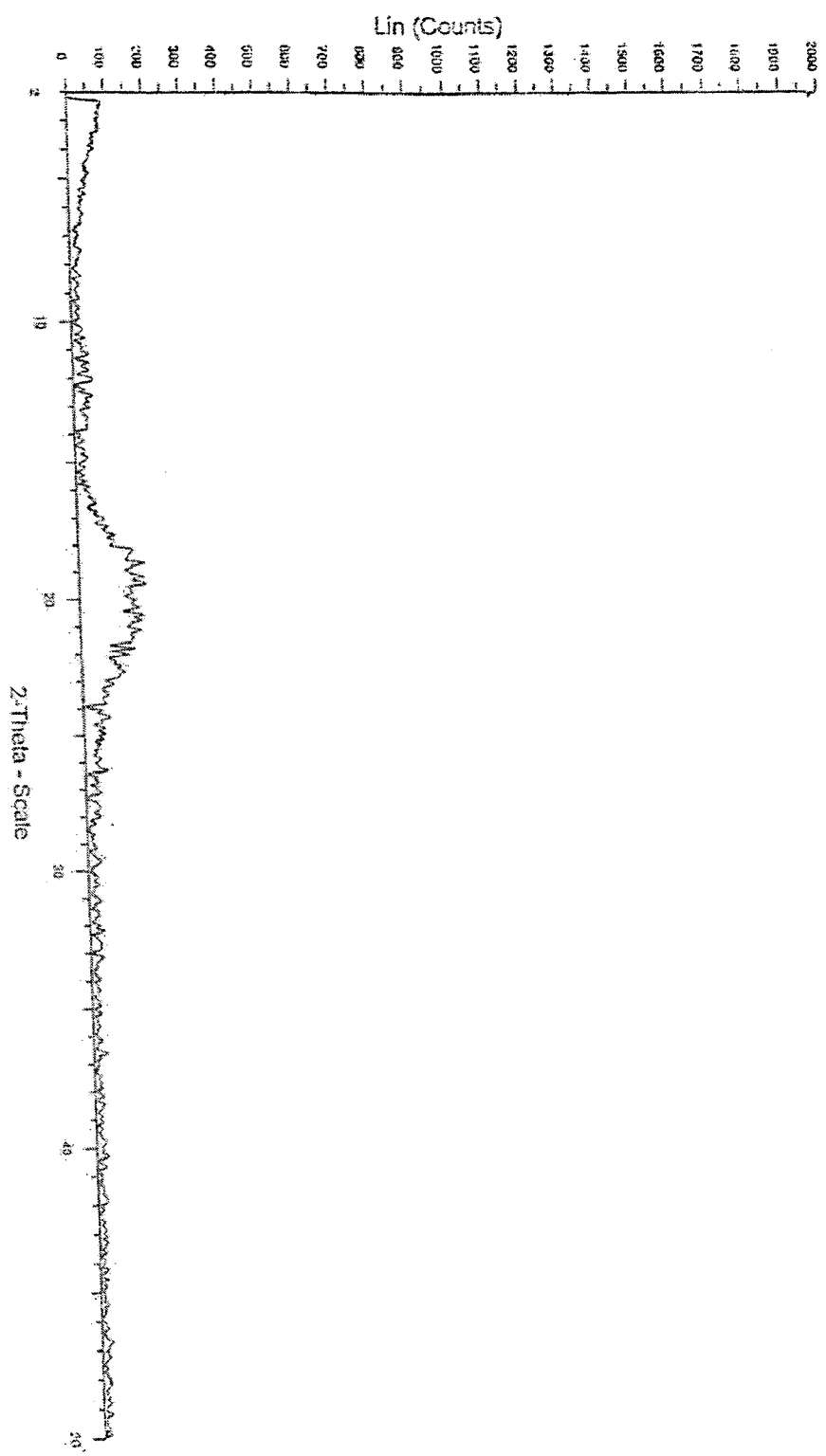
FIG. 2 is a x-ray powder diffraction spectrum of amorphous imatinib mesylate hydrate.

20. Amorphous imatinib mesylate hydrate of claim 19 characterized by a x-ray powder diffraction spectrum as in FIG. 2.

21. Amorphous imatinib mesylate hydrate of claim 19, produced according to the process described in claim 13.

22. A pharmaceutical composition comprising imatinib mesylate form H1 of claim 1 and a pharmaceutically acceptable carrier or diluent.

23. A pharmaceutical composition comprising imatinib mesylate hydrate of claim 9 and a pharmaceutically acceptable carrier or diluent.

24. A pharmaceutical composition comprising amorphous imatinib mesylate hydrate of claim 19 and a pharmaceutically acceptable carrier or diluent.

* * * * *

UNITED STATES PATENT AND TRADEMARK OFFICE
CERTIFICATE OF CORRECTION

PATENT NO. : 7,300,938 B2  Page 1 of 1
APPLICATION NO. : 10/518213
DATED : November 27, 2007
INVENTOR(S) : Bandi Parthasaradhi Reddy et al.

It is certified that error appears in the above-identified patent and that said Letters Patent is hereby corrected as shown below:

Title Page; should read;

(75) Inventors: Bandi Parthasaradhi Reddy, Hyderabad (IN); Kura Rathnakar Reddy, Hyderabad (IN); Rapolu Raji Reddy, Hyderabad (IN); Dasari Muralidhara Reddy, Hyderabad (IN); Kesireddy Subash Chander Reddy, Hyderabad (IN)

Signed and Sealed this

Eighteenth Day of March, 2008

JON W. DUDAS
*Director of the United States Patent and Trademark Office*